United States Patent [19]
Ichinohe et al.

[11] Patent Number: 6,114,560
[45] Date of Patent: Sep. 5, 2000

[54] METHOD FOR PREPARING A SHORT-CHAIN POLYSULFIDE SILANE MIXTURE

[75] Inventors: Shoji Ichinohe; Hideyoshi Yanagisawa, both of Usui-gun, Japan

[73] Assignee: Shin-Etsu Chem Co., Ltd., Tokyo, Japan

[21] Appl. No.: 09/326,587

[22] Filed: Jun. 7, 1999

[30] Foreign Application Priority Data

Jun. 8, 1998 [JP] Japan ................... 10-175391

[51] Int. Cl.⁷ ....................................................... C07F 7/08
[52] U.S. Cl. ............................................................... 556/427
[58] Field of Search ............................................. 556/427

[56] References Cited

U.S. PATENT DOCUMENTS

| | | |
|---|---|---|
| 3,808,951 | 5/1974 | Martin . |
| 4,507,490 | 3/1985 | Panster et al. ........................... 556/427 |
| 4,595,740 | 6/1986 | Panster ................. 556/427 X |
| 5,580,919 | 12/1996 | Agostini et al. . |
| 5,674,932 | 10/1997 | Agostini et al. . |
| 5,859,275 | 1/1999 | Munzenberg et al. ................... 556/427 |
| 5,977,394 | 11/1999 | Han et al. ............................... 556/427 |

FOREIGN PATENT DOCUMENTS

| | | |
|---|---|---|
| 47-29726 | 11/1972 | Japan . |
| 7-228588 | 8/1995 | Japan . |
| 8-259739 | 10/1996 | Japan . |

OTHER PUBLICATIONS

English Abstract for JP–A 7–228588.

*Primary Examiner*—Paul F. Shaver
*Attorney, Agent, or Firm*—Millen, White, Zelano & Branigan, P.C.

[57] ABSTRACT

A mixture of short-chain polysulfide silanes having the formula: $(RO)_3SiC_3H_6S_nC_3H_6Si(OR)_3$ wherein R is methyl or ethyl and n is a positive number having a distribution in the average range of $2.1 \leq n \leq 2.9$, is prepared by reacting one mole of an anhydrous sulfide of the formula: $M_2S$ or NS wherein M is an alkali metal or ammonium and N is an alkaline earth metal or zinc, with (n−1) mole of sulfur in an inert gas atmosphere and in a polar solvent, thereby forming polysulfide compounds, and reacting the polysulfide compounds with a halogenopropyltrialkoxysilane of the formula: $(RO)_3SiC_3H_6X$ wherein R is as defined above and X is a halogen atom. The method is simple to produce polysulfide silanes in high yields.

5 Claims, No Drawings

METHOD FOR PREPARING A SHORT-CHAIN POLYSULFIDE SILANE MIXTURE

This invention relates to a method for preparing a mixture of short-chain polysulfide silanes for use in silica-loaded tire compounds.

BACKGROUND OF THE INVENTION

In prior art silica-loaded tire compounds, bis(triethoxysilylpropyl) tetrasulfide is often used as a coupling agent for forming a bond between rubber and silica. This compound, however, has the problem that when milled with rubber and silica at elevated temperatures, it causes the blend to increase its Mooney viscosity to such an extent as to restrain subsequent working.

Then JP-A 8-259739 discloses a method for improving the workability of a rubber compound loaded with silica by blending bis(triethoxysilylpropyl) disulfide therein. When bis(triethoxysilylpropyl) disulfide is used alone, however, workability is improved at the sacrifice of low fuel consumption characteristic of the silica-loaded tires.

We thus paid attention to polysulfide silane mixtures and discovered that a good compromise is made between low fuel consumption and workability when a mixture of polysulfide silanes represented by the following general formula (1) is used.

$$(RO)_3SiC_3H_6S_nC_3H_6Si(OR)_3 \quad (1)$$

Herein n is a positive number having a distribution whose average is in the range: $2.1 \leq n \leq 2.9$, and R is methyl or ethyl.

With respect to the preparation of polysulfide silanes, JP-A 7-228588 discloses a method involving reacting $Na_2S$ with sulfur to produce polysulfides and, without isolating the polysulfides, continuously reacting the reaction product with a halogenoalkoxysilane. JP-A 7-228588, however, addresses the preparation of tetrasulfide silanes. No reference is made to short-chain polysulfide silanes of formula (1) wherein n is as defined above which can endow excellent properties to silica-loaded rubber tire compounds.

Another known method for preparing short-chain polysulfide silanes is by starting with tetrasulfide silanes and effecting desulfurization using sodium cyanide. Undesirably, sodium cyanide is toxic and the method requires an increased cost.

Short-chain polysulfide silanes can also be prepared by reacting pure sodium disulfide or sodium trisulfide with halogenoalkoxysilanes as disclosed in JP-A 47-29726. The preparation of pure sodium disulfide or sodium trisulfide requires a substantial cost, and consequently, the silane product becomes expensive.

SUMMARY OF THE INVENTION

Therefore, an object of the invention is to provide a novel and improved method for preparing a mixture of short-chain polysulfides in a simple, efficient and steady manner in high yields.

The present invention provides a method for preparing a mixture of short-chain polysulfide silanes having the following general formula (1):

$$(RO)_3SiC_3H_6S_nC_3H_6Si(OR)_3 \quad (1)$$

wherein R is methyl or ethyl and n is a positive number having a distribution, the average of the distribution being $2.1 \leq n \leq 2.9$. One mole of an anhydrous sulfide of the following formula (2) or (3):

$$M_2S \quad (2)$$

$$NS \quad (3)$$

wherein M is an alkali metal or ammonium and N is an alkaline earth metal or zinc, is reacted with (n−1) mole of sulfur in an inert gas atmosphere and in a polar solvent wherein n is a positive number of from 2.1 to 2.9, thereby forming polysulfide compounds. Without isolating the polysulfide compounds, the reaction product is reacted with a halogenopropyltrialkoxysilane of the following general formula (4):

$$(RO)_3SiC_3H_6X \quad (4)$$

wherein R is as defined above and X is a halogen atom. The method ensures that a mixture of short-chain polysulfides is efficiently produced in high yields. The short-chain polysulfide silane mixture is effective for achieving both low fuel consumption and workability when blended in silica-loaded tire compounds.

The anhydrous sulfide may be a product formed by heat treating in vacuum hydrous sodium sulfide represented by $Na_2S \cdot mH_2O$; by dissolving hydrous sodium sulfide represented by $Na_2S \cdot mH_2O$ in a polar solvent, and distilling off the solvent; or by reacting NaOR' wherein R' is methyl or ethyl with $H_2S$, preferably at a molar ratio of 2:1. Such a product may be used in the subsequent step (reaction with sulfur) without isolation. Then the reaction can be effectively carried out at a low cost.

DETAILED DESCRIPTION OF THE INVENTION

According to the invention, a mixture of short-chain polysulfide silanes having the following general formula (1):

$$(RO)_3SiC_3H_6S_nC_3H_6Si(OR)_3 \quad (1)$$

wherein R is methyl or ethyl and n is a positive number having a distribution, the average of the distribution being $2.1 \leq n \leq 2.9$, is prepared by reacting one mole of an anhydrous sulfide of the following formula (2) or (3):

$$M_2S \quad (2)$$

$$NS \quad (3)$$

wherein M is an alkali metal or ammonium and N is an alkaline earth metal or zinc, with (n−1) mole of sulfur in an inert gas atmosphere and in a polar solvent wherein n is a positive number of from 2.1 to 2.9, thereby forming polysulfide compounds, and then reacting the polysulfide compounds, without isolation, with a halogenopropyltrialkoxysilane of the following general formula (4):

$$(RO)_3SiC_3H_6X \quad (4)$$

wherein R is as defined above and X is a halogen atom.

The first step of reacting an anhydrous sulfide of formula (2) or (3) with sulfur yields polysulfide compounds of the following formula (2') or (3'):

$$M_2S_n \quad (2')$$

$$NS_n \quad (3')$$

wherein M, N, and n are as defined above. According to the invention, without isolating the polysulfide compounds, the reaction mixture is directly subject to the subsequent reaction with a halogenopropyltrialkoxysilane of formula (4).

Exemplary of the anhydrous sulfide of formula (2) or (3) are $Na_2S$, $K_2S$, $Li_2S$, $(NH)_2S$, CaS, MgS, and ZnS, with $Na_2S$ being especially preferable.

The anhydrous sulfide of formula (2) or (3) may be prepared by dehydration of a hydrous metal sulfide or reaction of a metal alcoholate with hydrogen sulfide. More specifically, $Na_2S$ may be prepared by heat treating in vacuum hydrous sodium sulfide represented by $Na_2S.mH_2O$ wherein m is from 1 to 20, or dissolving hydrous sodium sulfide in a polar solvent such as toluene or an alcohol (e.g., ethanol or methanol), and distilling off the polar solvent. Alternatively, $Na_2S$ is prepared by dissolving a sodium alcoholate represented by NaOR' wherein R' is methyl or ethyl in an alcohol (e.g., ethanol or methanol), and blowing $H_2S$ into the solution for reaction.

In the first step of reacting the anhydrous sulfide compound of formula (2) or (3) with sulfur to form anhydrous polysulfide compounds (or a mixture of metal polysulfides), 1 mole of the anhydrous sulfide compound is reacted with (n−1) mole of sulfur wherein n is as defined above. This reaction is usually carried out in a solvent.

Herein, the solvent permitting the metal sulfide to be partially dissolved in the reaction system is advantageously used. Exemplary solvents include aliphatic solvents such as pentane and hexane, aromatic solvents such as benzene, toluene and xylene, ethers such as diethyl ether and dibenzyl ether, esters, and ketones. More useful solvents are alcohols, for example, methanol, ethanol, propanol, butanol, benzyl alcohol, and phenol, with methanol and ethanol being most advantageous.

The reaction temperature may range from room temperature to 150° C., more preferably from room temperature to 100° C. Solvent reflux conditions, especially ethanol reflux conditions are appropriate. Unless the metal sulfide is dissolved in the reaction system, the reaction between sulfur and metal sulfide does not proceed to a full extent, leaving some sulfur unreacted and failing to produce a mixture of metal polysulfides having the desired distribution.

In the second step, the thus obtained mixture of metal polysulfides is subject to reaction, without isolation. More specifically, a halogenopropyltrialkoxysilane is added for reaction to the reaction mixture containing the thus formed metal polysulfides and the solvent, that is, the solution of metal polysulfide mixture in the reaction vessel.

The halogenopropyltrialkoxysilane is of formula (4):

$(RO)_3SiC_3H_6X$                            (4)

wherein X is a halogen atom such as Cl, Br or I, preferably Cl or Br, and R is methyl or ethyl. Examples of the compound of formula (4) include $ClC_3H_6Si(OC_2H_5)_3$, $ClC_3H_6Si(OCH_3)_3$, and $BrC_3H_6Si(OC_2H_5)_3$.

The solvent advantageously used in this reaction may be the same as the solvent used in the preparation of polysulfides. Any of the above-mentioned solvents may be used, with methanol and ethanol being most preferred. Most often, the metal polysulfide mixture is formed in methanol or ethanol solvent and as such, sequentially reacted with the halogenopropyltrialkoxysilane.

The reaction temperature may range from room temperature to 150° C., more preferably from 60 to 100° C. Solvent reflux conditions, especially ethanol reflux conditions are appropriate. The reaction time is usually 1 to 20 hours although reaction may proceed to completion within 1 to 5 hours under ethanol reflux conditions.

After the completion of reaction, the solvent is distilled off under vacuum and the salt formed is filtered off, obtaining the desired mixture of short-chain polysulfide silanes of formula (1) in high yields.

With respect to the short-chain polysulfide silane mixture of formula (1), if n is less than 2.1, tires having the polysulfide silane mixture blended therein are unsatisfactory in fuel consumption reduction. If n is more than 2.9, the rubber milled together with the polysulfide silane mixture at elevated temperature becomes poorly workable. The more preferred range of n is from 2.2 to 2.8, within which the best compromise between low fuel consumption and workability is found. With respect to the distribution, the content of disulfide silanes in the polysulfide silane mixture should preferably be not more than 80% by weight, more preferably 30 to 80% by weight. The content of monosulfide silanes is preferably not more than 10% by weight.

There has been described a method for preparing a mixture of short-chain polysulfides of formula (1) in a simple and steady manner in high yields.

EXAMPLE

Examples of the invention are given below by way of illustration and not by way of limitation.

First the preparation of anhydrous sodium sulfide is described.

Preparation Example 1

$Na_2S.5H_2O$, 168.1 g (1.00 mol), was dehydrated by drying the system by means of a vacuum dryer, evacuating to 20 Torr, and heating at 90° C. for one hour and then at 120° C. for 8 hours.

Preparation Example 2

A 2-liter flask equipped with a nitrogen inlet tube, Dimroth condenser, ester adapter, thermometer, and dropping funnel was purged with nitrogen, and charged with 168.1 g (1.00 mol) of $Na_2S.5H_2O$ together with 400 g of toluene and 1,000 g of ethanol as the solvent. The system was heated and agitated. While the temperature was slowly elevated, the solvent was distilled off. When the internal temperature reached 110° C. and the amount of the solvent distilled off summed to 1,200 g, heating was interrupted. As a consequence, the sodium sulfide was dehydrated to $Na_2S$, to which 400 g of ethanol was added before it was subject to the subsequent reaction.

Preparation Example 3

A 2-liter flask as used in Preparation Example 2 was purged with nitrogen, and charged with 648 g of a 21.0% $NaOC_2H_5$ ethanol solution (2.0 mol of $NaOC_2H_5$). After the admission of nitrogen gas was interrupted, 34.1 g (1.0 mol) of $H_2S$ gas was blown into the solution at room temperature over 30 minutes. Agitation was continued for 2 hours. The formation of $Na_2S$ in the flask was confirmed. Without further treatment, this was subject to the subsequent reaction.

Example 1

A 2-liter flask was charged with 78 g (1 mol) of anhydrous sodium sulfide obtained in Preparation Example 1, 48 g (1.5 mol) of sulfur and 300 g of ethanol and heated in a nitrogen gas atmosphere until ethanol refluxed. Next, 481 g (2 mol) of chloropropyltriethoxysilane was added dropwise and the reaction mixture was ripened for 5 hours under ethanol reflux. Thereafter, the ethanol was distilled off in vacuum and the sodium chloride formed filtered off, leaving 450 g of polysulfide silanes having an average sulfide chain of 2.5 (yield 92%). On analysis by supercritical chromatography, this was found to be a mixture of polysulfide silanes having the following composition.

| | |
|---|---|
| monosulfide silane | 2 wt% |
| disulfide silane | 54 wt% |
| trisulfide silane | 30 wt% |
| tetrasulfide silane | 11 wt% |
| penta and poly-sulfide silanes | 3 wt% |

Example 2

To the solution of anhydrous sodium sulfide obtained in Preparation Example 2 in 400 g of ethanol was added 35 g (1.1 mol) of sulfur. The mixture was heated until ethanol refluxed. This was followed by the same procedure as in Example 1, obtaining 440 g of polysulfide silanes having an average sulfide chain of 2.1 (yield 92%). On analysis by supercritical chromatography, this was found to be a mixture of polysulfide silanes having the following composition.

| | |
|---|---|
| monosulfide silane | 9 wt% |
| disulfide silane | 72 wt% |
| trisulfide silane | 15 wt% |
| tetra and poly-sulfide silanes | 4 wt% |

Example 3

The procedure of Example 1 was repeated except that the reaction mixture obtained in Preparation Example 3 was used, obtaining 440 g of polysulfide silanes having an average sulfide chain of 2.5 (yield 90%). On analysis by supercritical chromatography, this was found to be a mixture of polysulfide silanes in the following composition.

| | |
|---|---|
| monosulfide silane | 3 wt% |
| disulfide silane | 53 wt% |
| trisulfide silane | 32 wt% |
| tetrasulfide silane | 10 wt% |
| penta and poly-sulfide silanes | 2 wt% |

Comparative Examples 1–3

In accordance with the method of JP-A 8-259739, $(C_2H_5O)_3SiC_3H_6S_2C_3H_6Si(OC_2H_5)_3$ was synthesized by oxidizing $(C_2H_5O)_3SiC_3H_6SH$ in the presence of manganese dioxide (Comparative Example 1).

Single compounds $Na_2S_3$ and $Na_2S_4$ each were purified by a sublimation technique and reacted with chloropropyltriethoxysilane to produce single compounds: $(C_2H_5O)_3SiC_3H_6S_3C_3H_6Si(OC_2H_5)_3$ (Comparative Example 2) and $(C_2H_5O)_3SiC_3H_6S_4C_3H_6Si(OC_2H_5)_3$ (Comparative Example 3).

The polysulfide silanes of Examples 1 to 3 and Comparative Examples 1 to 3 were examined for a balance of low fuel consumption and workability by the following test. The results are shown in Table 1.

The low fuel consumption was rated in terms of hysteresis loss (or heat generation). A rubber compound obtained in the workability test was measured for tanδ by a viscoelasticity spectrometer (Iwamoto Mfg. K.K.). A sample with low tanδ was rated OK, and a sample with greater tanδ rated NG.

In the workability test, a rubber compound was prepared by milling at 150° C. 100 parts by weight of styrene-butadiene rubber, 60 parts by weight of silica (Nipsil AQ by Nippon Silica K.K.), and 6 parts by weight of the polysulfide silane, and measured for Mooney viscosity ($ML_{1+4}$) at 130° C. A rubber compound which experienced little increase of Mooney viscosity and remained well workable was rated "Good," a rubber compound which experienced an increase of Mooney viscosity and remained fairly workable was rated "Fair," and a rubber compound which experienced a substantial increase of Mooney viscosity (partially gelled) and became difficult to work was rated "Poor."

TABLE 1

| | Low fuel consumption | Workability |
|---|---|---|
| Example 1 | OK | Good |
| Example 2 | OK | Good |
| Example 3 | OK | Good |
| Comparative Example 1 | NG | Good |
| Comparative Example 2 | OK | Fair |
| Comparative Example 3 | OK | Poor |

Japanese Patent Application No. 10-175391 is incorporated herein by reference.

Although some preferred embodiments have been described, many modifications and variations may be made thereto in the light of the above teachings. It is therefore to be understood that within the scope of the appended claims, the invention may be practiced otherwise than as specifically described.

We claim:

1. A method for preparing a mixture of short-chain polysulfide silanes having the following general formula (1):

$$(RO)_3SiC_3H_6S_nC_3H_6Si(OR)_3 \quad (1)$$

wherein R is methyl or ethyl and n is a positive number having a distribution, the average of the distribution being $2.1 \leq n \leq 2.9$, comprising the steps of:

reacting one mole of an anhydrous sulfide of the following formula (2) or (3):

$$M_2S \quad (2)$$

$$NS \quad (3)$$

wherein M is an alkali metal or ammonium and N is an alkaline earth metal or zinc, with (n−1) mole of sulfur in an inert gas atmosphere and in a polar solvent wherein n is a positive number of from 2.1 to 2.9, thereby forming polysulfide compounds, and reacting the polysulfide compounds, without isolation, with a halogenopropyltrialkoxysilane of the following general formula (4):

$$(RO)_3SiC_3H_6X \quad (4)$$

wherein R is as defined above and X is a halogen atom.

2. The method of claim 1 wherein said anhydrous sulfide has been formed by heat treating in vacuum hydrous sodium sulfide represented by $Na_2S.mH_2O$.

3. The method of claim 1 wherein said anhydrous sulfide has been formed by dissolving hydrous sodium sulfide represented by $Na_2S.mH_2O$ in a polar solvent, and distilling off the solvent.

4. The method of claim 1 wherein said anhydrous sulfide has been formed by reacting NaOR' wherein R' is methyl or ethyl with $H_2S$.

5. The method of claim 1 wherein said mixture of short-chain polysulfide silanes contains up to 80% by weight of disulfide silanes.

* * * * *